(12) United States Patent
Son

(10) Patent No.: US 12,227,747 B2
(45) Date of Patent: Feb. 18, 2025

(54) COMPOSITION COMPRISING APTAMER AS ACTIVE INGREDIENT FOR TREATMENT AND PREVENTION OF DEGENERATIVE BRAIN DISEASE

(71) Applicant: Nexmos Co., LTD, Yongin-si (KR)

(72) Inventor: In Sik Son, Seongnam-si (KR)

(73) Assignee: NEXMOS Co., Ltd., Yongin-si (KR)

( * ) Notice: Subject to any disclaimer, the term of this patent is extended or adjusted under 35 U.S.C. 154(b) by 760 days.

(21) Appl. No.: 17/292,710

(22) PCT Filed: Oct. 11, 2019

(86) PCT No.: PCT/KR2019/013383
§ 371 (c)(1),
(2) Date: May 10, 2021

(87) PCT Pub. No.: WO2020/101181
PCT Pub. Date: May 22, 2020

(65) Prior Publication Data
US 2022/0002729 A1 Jan. 6, 2022

(30) Foreign Application Priority Data

Nov. 14, 2018 (KR) .......................... 10-2018-0140074
May 13, 2019 (KR) .......................... 10-2019-0055758

(51) Int. Cl.
C12N 15/115 (2010.01)
A61K 31/375 (2006.01)
A61K 31/713 (2006.01)
A61P 25/16 (2006.01)

(52) U.S. Cl.
CPC .......... *C12N 15/115* (2013.01); *A61K 31/375* (2013.01); *A61K 31/713* (2013.01); *A61P 25/16* (2018.01)

(58) Field of Classification Search
CPC ................ C12N 15/113; C12N 15/115; C12N 2310/16; A61P 25/16; A61P 25/28

USPC ..................... 435/6.1, 91.1, 91.31, 455, 458; 514/44 A; 536/23.1, 24.5
See application file for complete search history.

(56) References Cited

U.S. PATENT DOCUMENTS

| 10,201,489 B2 * | 2/2019 | Son ......................... C08G 77/18 |
| 10,655,131 B2 * | 5/2020 | Son ......................... C12N 15/115 |
| 2019/0078094 A1 | 3/2019 | Son |

FOREIGN PATENT DOCUMENTS

| EP | 3530260 | 8/2019 | |
| EP | 3530260 A1 * | 8/2019 | ........... A45D 44/002 |
| KR | 1020190050372 | 5/2019 | |
| WO | 2018074763 | 4/2018 | |

OTHER PUBLICATIONS

Minkyung Song et al., "Nuroprotective effect of Aptamin-C in 1-methyl-4-phenyl-1,2,3,6-tetrahydropyridine (MPTP) Induced Parkinson's disease mice model", IBRO Reports, vol. 6 p. S96 P02.21, Sep. 2019.
Adriana Covarrubias-Pinto et al., "Old Things New View: Assorbic Acid Protects the Brain in Neurodegenerative Disorders", international journal of molecular sciences, vol. 16, pp. 28194-28217, 2015.
Morgana Moretti et al.,, "Preventive and therapeutic potential of ascorbic acid in neurodegenerative diseases", CNS Neuroscience & Therapeutics, vol. 23, pp. 921-929, 2017.
Office Action for Japan Patent Application No. 2021-526288, dated Jun. 21, 2022.

* cited by examiner

*Primary Examiner* — Jane J Zara

(57) ABSTRACT

The present invention relates to a composition for treating and preventing degenerative brain diseases comprising a complex of vitamin C and an aptamer binding to the vitamin C as an active ingredient, and the composition of the present invention has improved and therapeutic effects in a Parkinson's disease experimental model and so the composition of the present invention can be used as medicines and health functional foods for patients with degenerative brain diseases including Parkinson's disease.

5 Claims, 12 Drawing Sheets

Specification includes a Sequence Listing.

[Fig. 1]
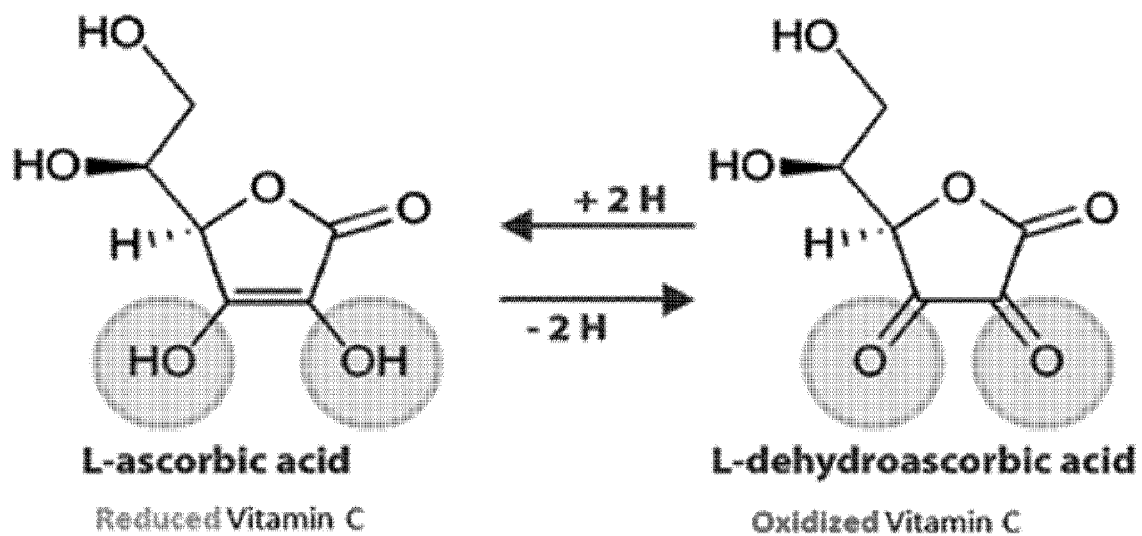

[Fig. 2]
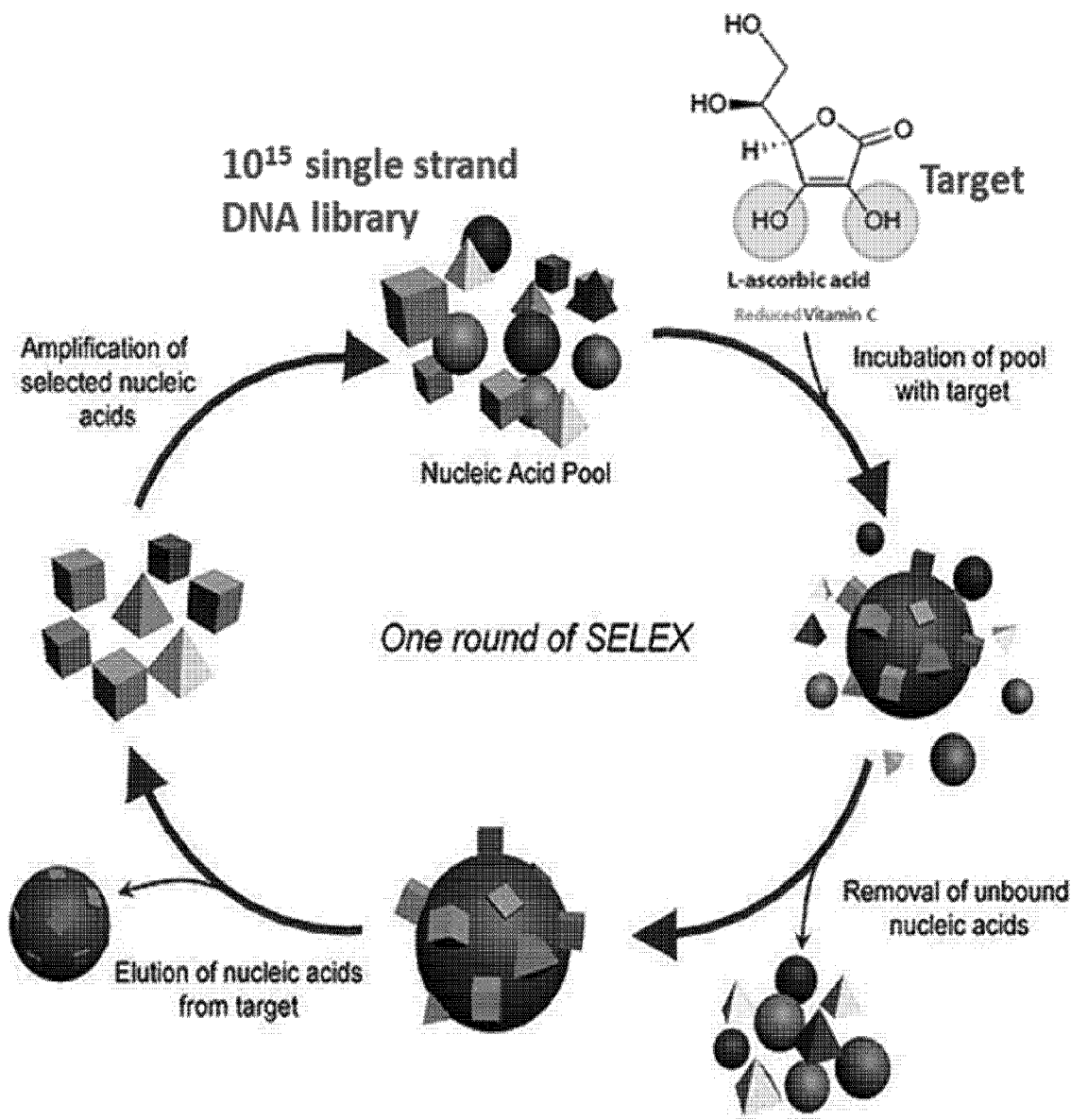

[Fig. 3]
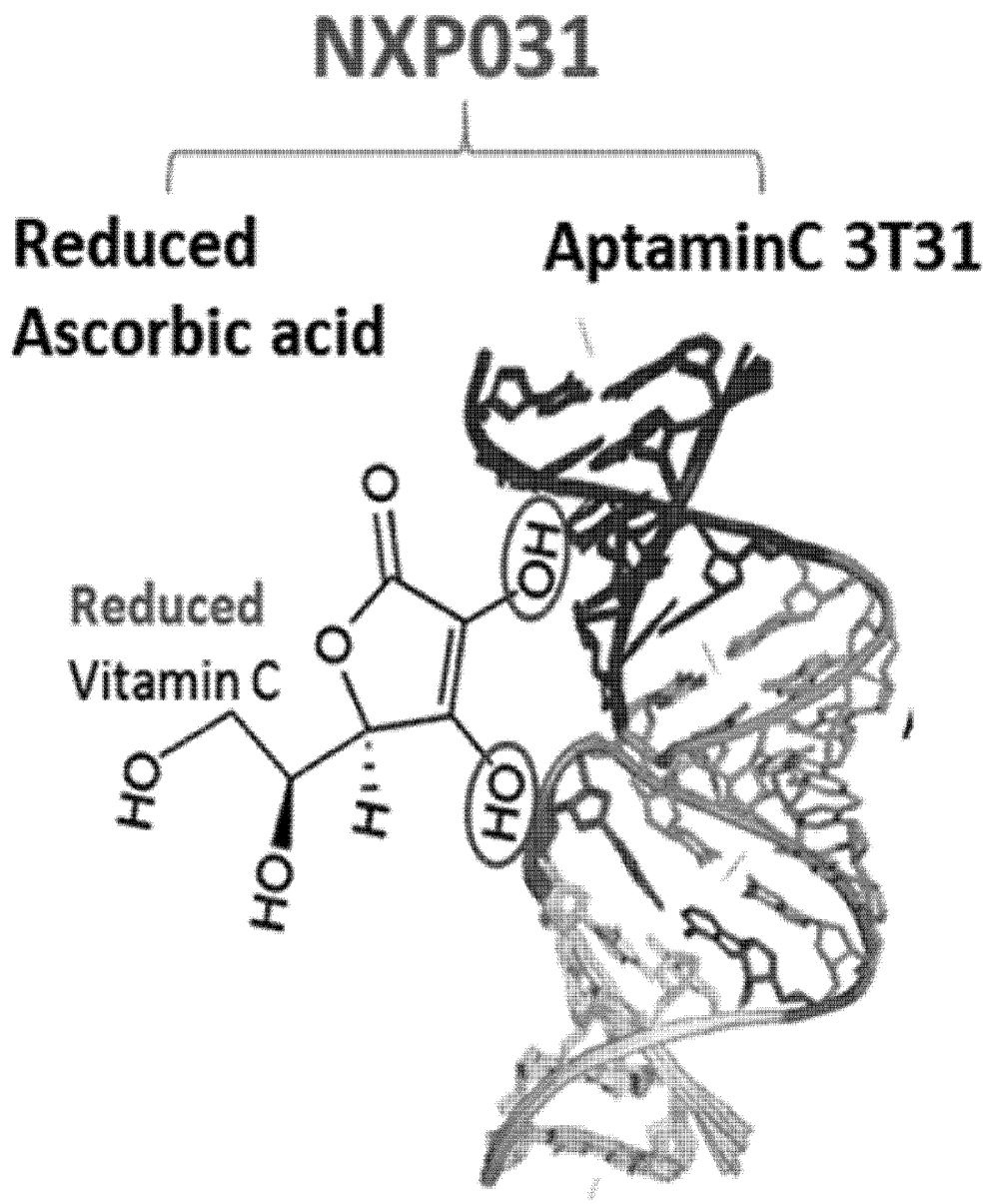

[Fig. 4]
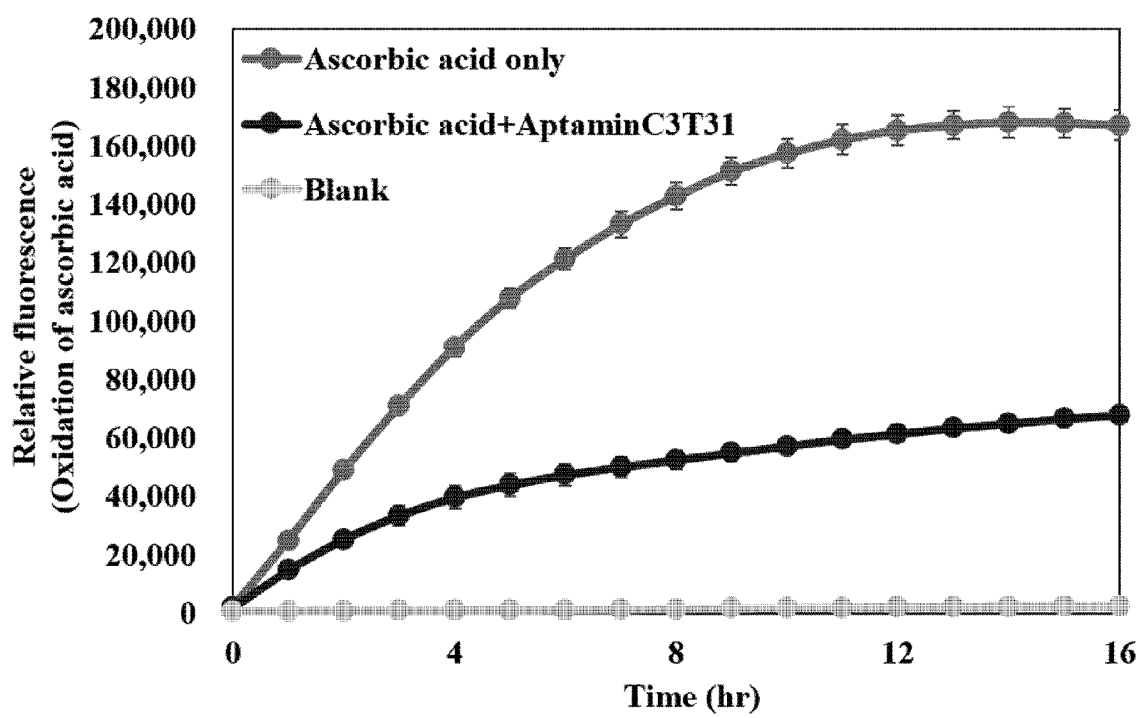

[Fig. 5]
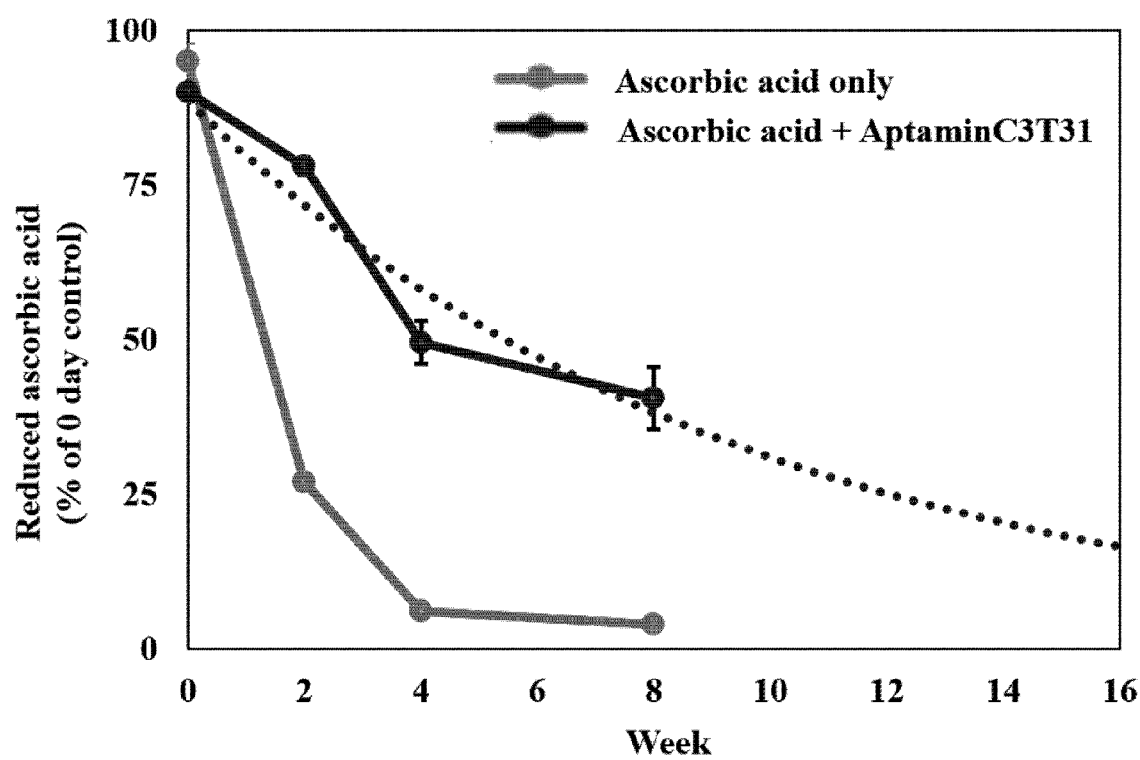

[Fig. 6]
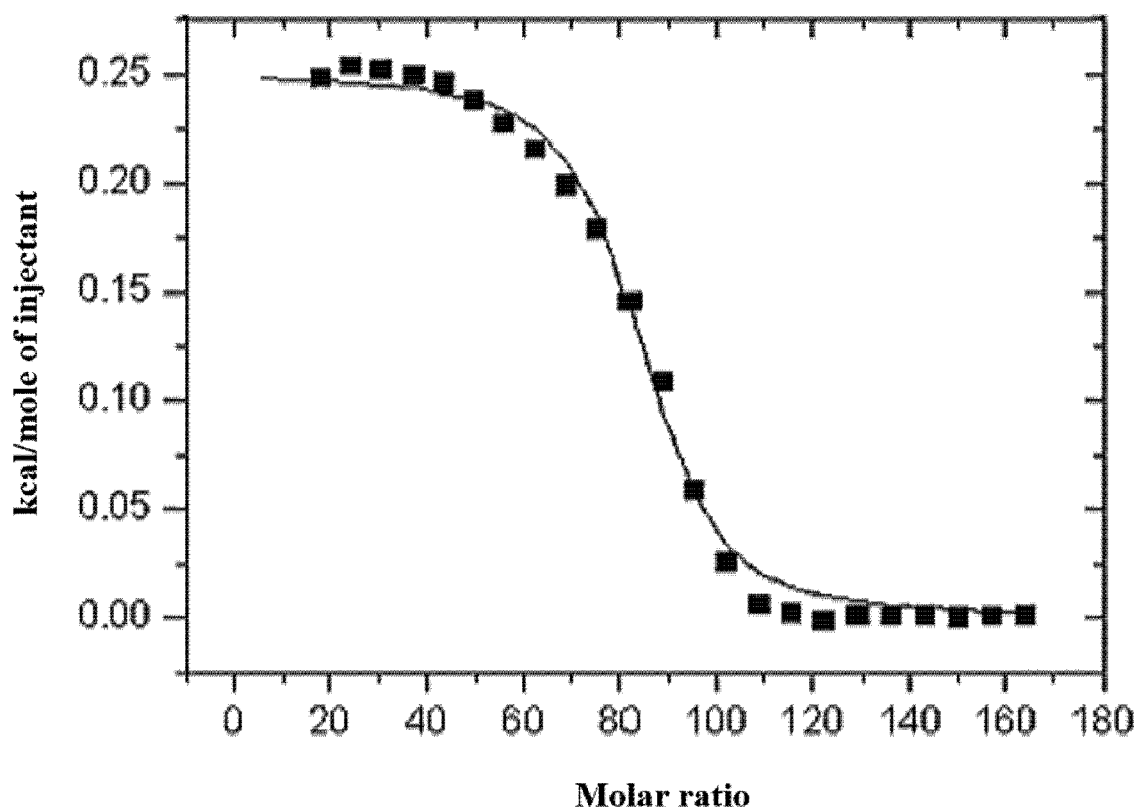

[Fig. 7]
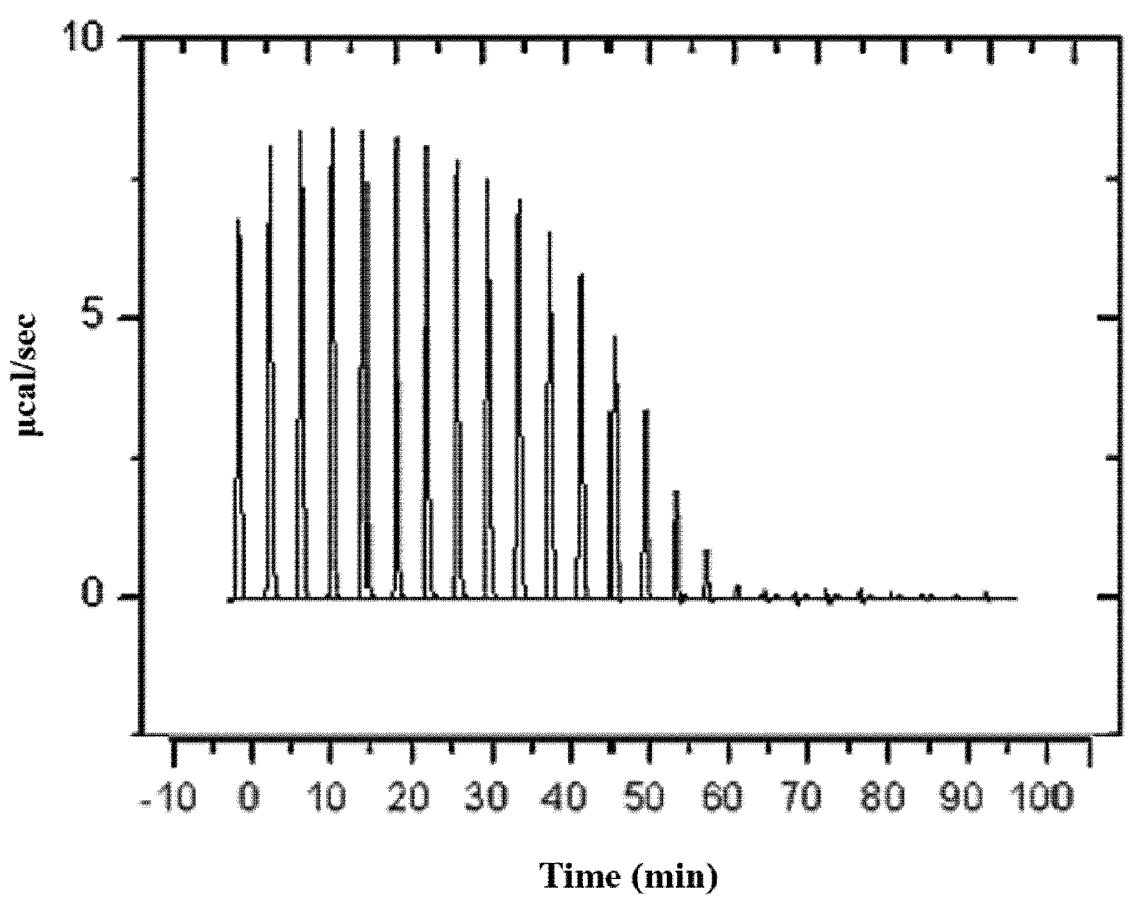

[Fig. 8]
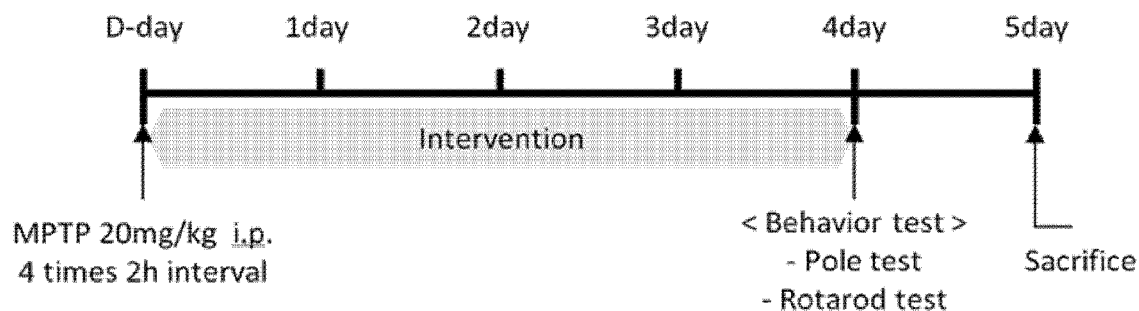
[Fig. 9]
Body weight
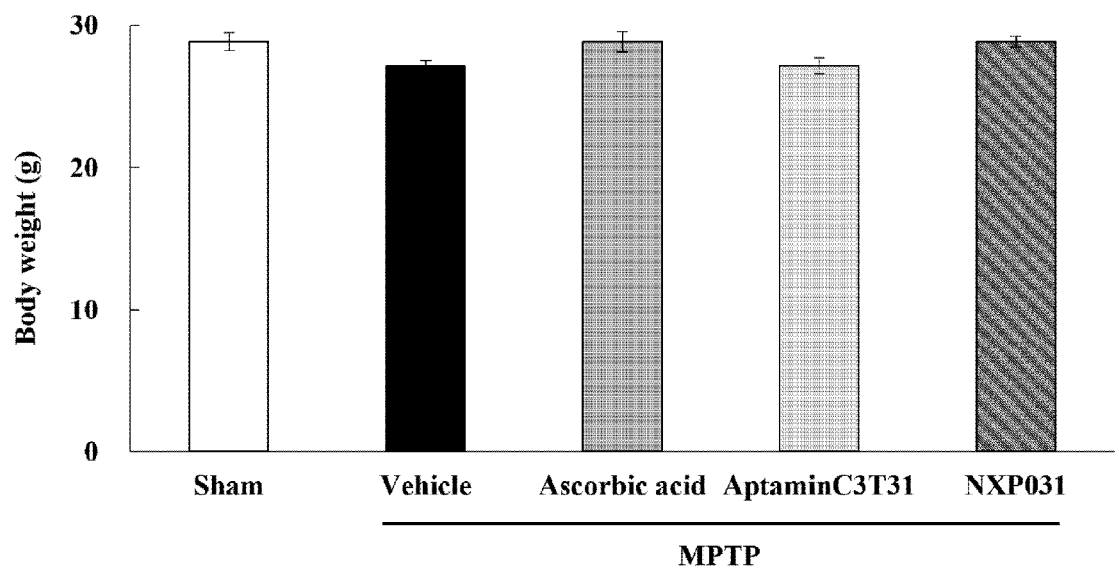

[Fig. 10]
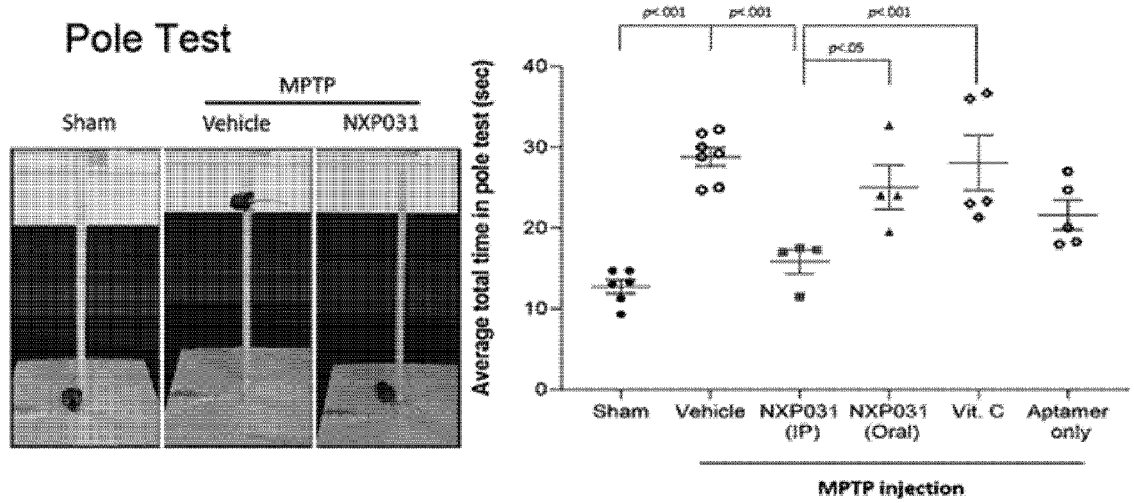
[Fig. 11]
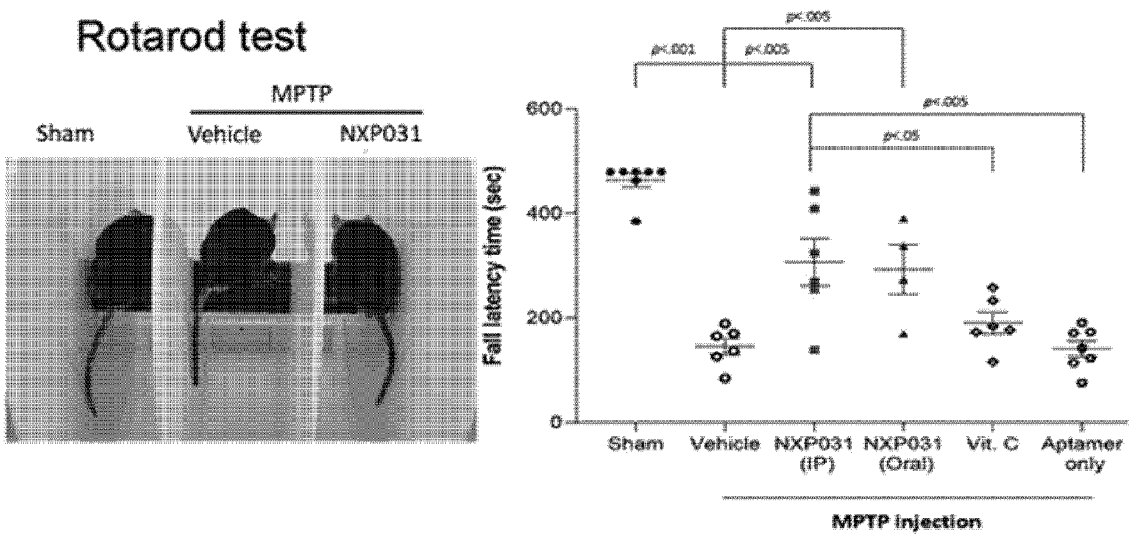

[Fig. 12]
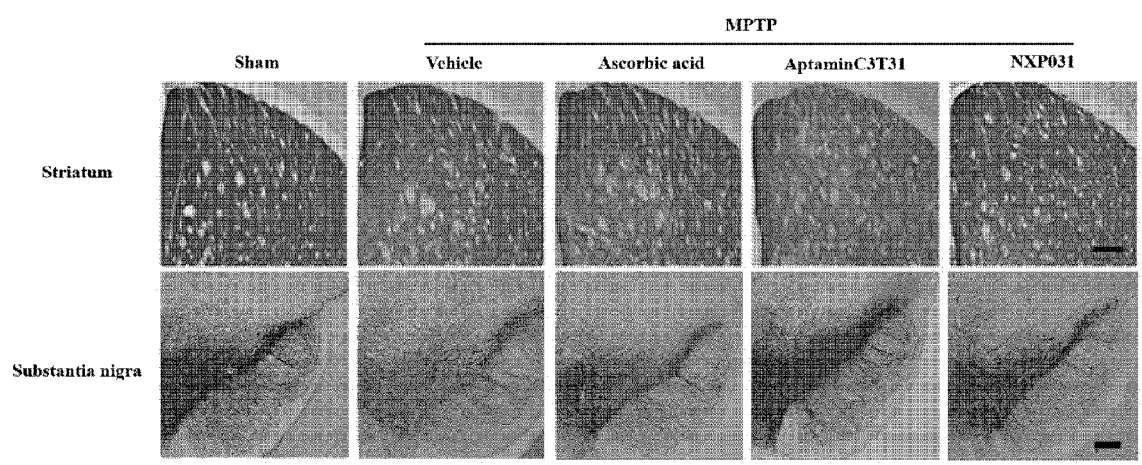

[Fig. 13]
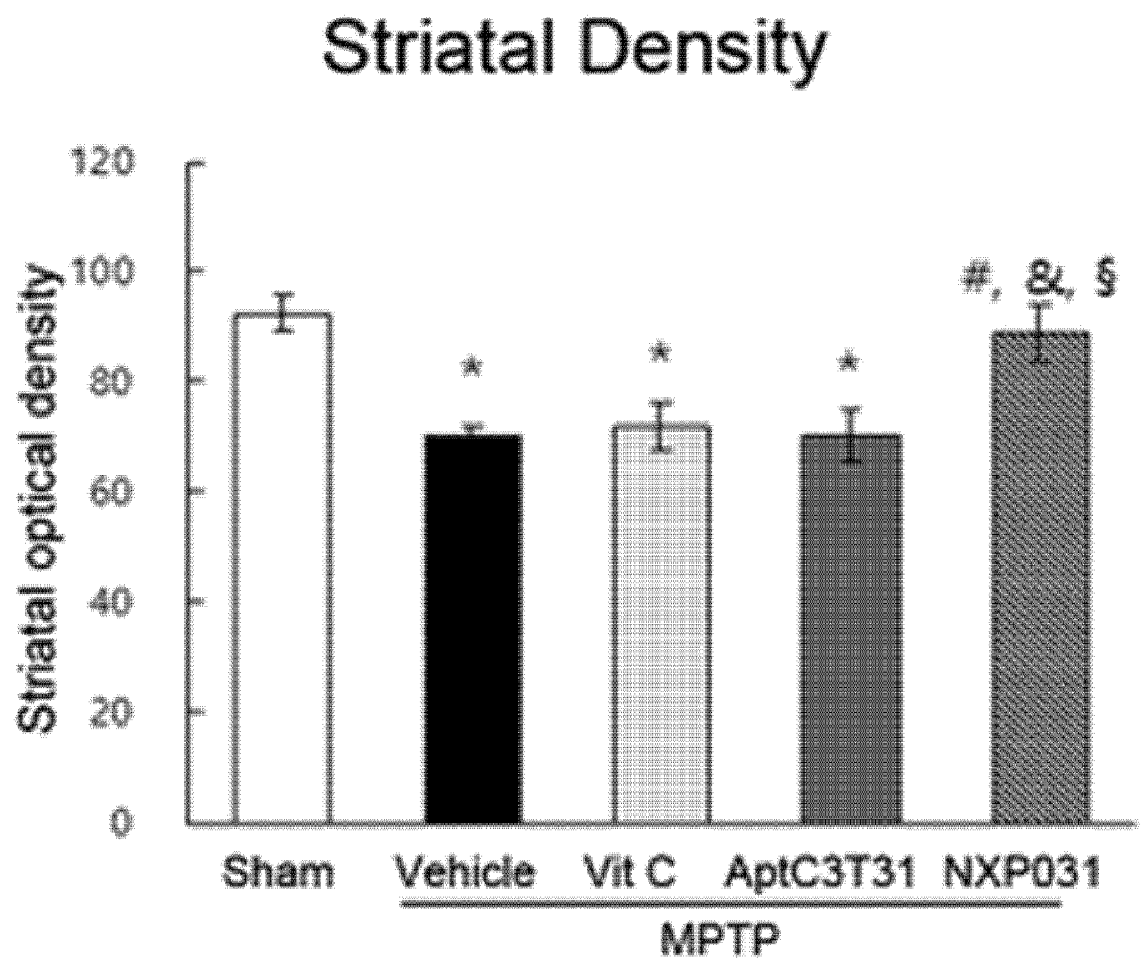

[Fig. 14]
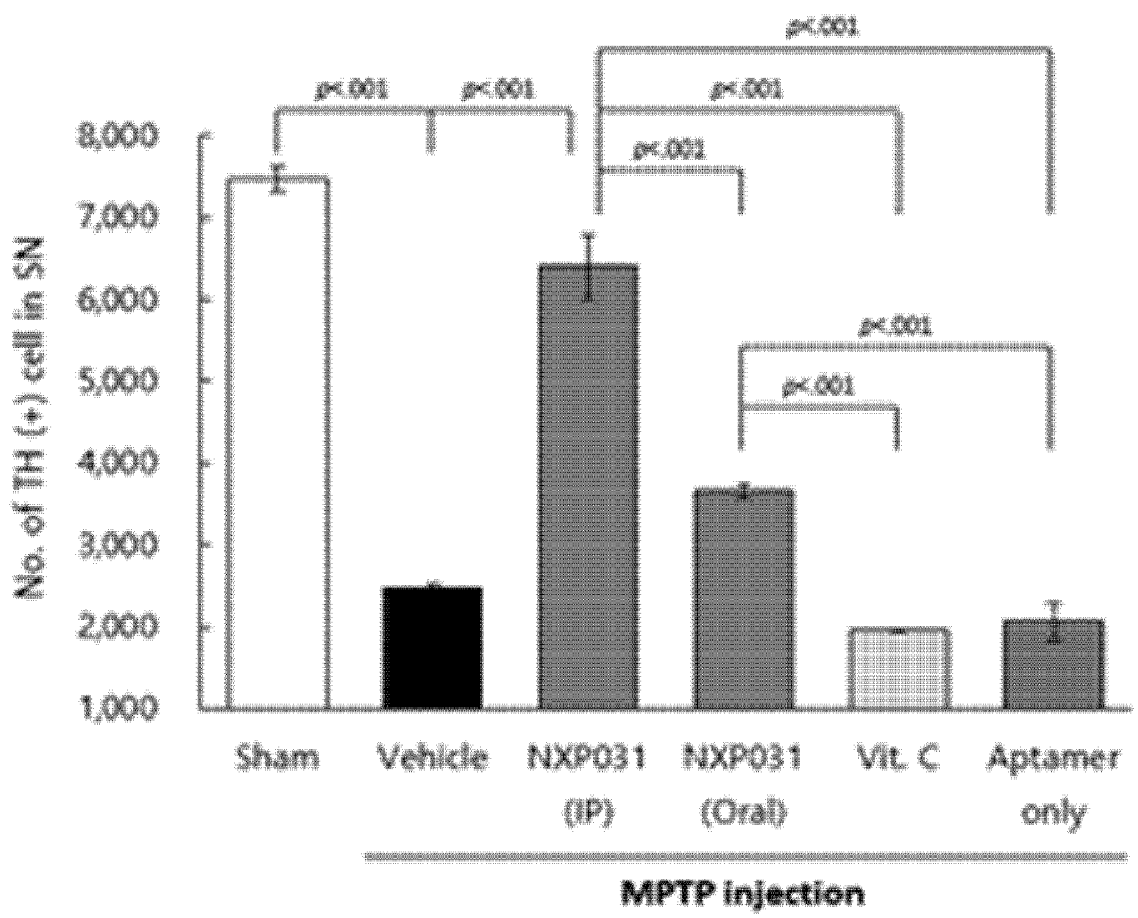

SEQUENCE LISTING

```
<160> NUMBER OF SEQ ID NOS: 1

<210> SEQ ID NO 1
<211> LENGTH: 32
<212> TYPE: DNA
<213> ORGANISM: Artificial Sequence
```

-continued

```
<220> FEATURE:
<223> OTHER INFORMATION: aptamer

<400> SEQUENCE: 1
gtggaggcgg tggccagtct cgcggtggcg gc                                32
```

COMPOSITION COMPRISING APTAMER AS ACTIVE INGREDIENT FOR TREATMENT AND PREVENTION OF DEGENERATIVE BRAIN DISEASE

TECHNICAL FIELD

The present invention relates to a composition for treating and preventing degenerative brain diseases comprising an aptamer that binds to vitamin C as an active ingredient.

STATEMENT OF COMMON OWNERSHIP

Pursuant to 35 USC § 102(b)(2)(C) and MPEP § 2146.02 (I), Applicant hereby states that this application, U.S. Non-provisional patent application Ser. No. 16/148,236, not later than the effective filing date of this application, were owned by or subject to an obligation of assignment to the same person (NEXMOS Co., Ltd.).

BACKGROUND ART

Degenerative brain disease is an aging-related disease defined in relation to the gradual loss of specific neuronal cell populations and protein aggregates, and it is divided into Alzheimer's disease, Parkinson's disease, and amyotrophic lateral sclerosis etc. in consideration of major clinical symptoms and invading brain regions. A common characteristic of these diseases is that although the underlying treatment is difficult and the cause of the disease is not clear, oxidative stress, which can lead to dysfunction or death of nerve cells, contributes to the pathogenesis of the disease. The brain is particularly susceptible to oxidative stress. The brain is an organ that requires a high concentration of metal ions in order to maintain many functions. It lacks the ability to process oxidative stress and has little regenerative ability, so it cannot revive neurons once died.

Therefore, there is a growing need for the development of a new therapeutic agent for preventing degenerative brain diseases caused by the death of nerve cells due to oxidative stress.

PRIOR PATENT LITERATURE

Korean Patent Publication No. 10-2013-0139771

DISCLOSURE

Technical Problem

The present invention solves the above problems and is due to the necessity of the above, an object of the present invention is to provide a novel composition having an effect of treating and preventing degenerative brain diseases.

Technical Solution

In order to achieve the above object, the present invention provides a composition for treating and preventing degenerative brain diseases, comprising an aptamer that binds to vitamin C as an active ingredient.

In one embodiment of the present invention, the composition preferably further comprises vitamin C, but is not limited thereto.

In another embodiment of the present invention, the aptamer is preferably composed of the nucleotide sequence shown in SEQ ID NO: 1, but all aptamer sequences capable of achieving the effects of the present invention through one or more substitutions, deletions, translocations, and additions to the nucleotide sequence are also included in the scope of the present invention.

In another embodiment of the present invention, the mixing ratio of vitamin C and aptamer is preferably in the range of 10:1 to 500:1 by weight, and more preferably in the range of 20:1 to 50:1, but is not limited thereto.

In one embodiment of the present invention, the composition preferably has a nerve cell protective effect, but is not limited thereto.

In the present invention, the degenerative brain diseases include stroke, stroke, dementia, Alzheimer's disease, Parkinson's disease, Huntington's disease, multiple sclerosis, and amyotrophic lateral sclerosis etc. Brain disease refers to a disease caused by the death of cranial nerve cells, which are the most important for the transmission of information in the cranial nerve system, problems with the formation or function of synapses that transmit information between cranial nerve cells and cranial nerve cells, and abnormal symptoms or decrease in electrical activity of the cranial nerve.

In one embodiment of the present invention, the degenerative brain disease is preferably Parkinson's disease, but is not limited thereto.

The route of administration of the pharmaceutical composition according to the present invention is not limited thereto, but includes oral, intravenous, intramuscular, intraarterial, intramedullary, intrathecal, intracardiac, transdermal, subcutaneous, intraperitoneal, intranasal, intestinal, topical, sublingual or rectal. Oral or parenteral administration is preferred. The term "parenteral" as used herein includes subcutaneous, intradermal, intravenous, intramuscular, intraarticular, intrasynovial, intrasternal, intrathecal, intralesional and intracranial injection or infusion techniques. The pharmaceutical composition of the present invention may also be administered in the form of suppositories for rectal administration.

The pharmaceutical composition of the present invention may be orally administered in any orally acceptable dosage form including, but not limited to, capsules, tablets, and aqueous suspensions and solutions. In the case of tablets for oral use, carriers commonly used include lactose and corn starch. Lubricating agents such as magnesium stearate are also typically added. For oral administration in capsule form, useful diluents include lactose and dried corn starch. When aqueous suspensions are administered orally, the active ingredient is combined with emulsifying and suspending agents. If necessary, sweetening and/or flavoring and/or coloring agents may be added.

The pharmaceutical composition of the present invention can be varied in various ways depending on a number of factors including the activity of the compound of the present invention used, age, weight, general health, sex, formulation, administration time, route of administration, excretion rate, drug formulation, and the severity of the specific disease to be prevented or treated. The pharmaceutical composition according to the present invention may be formulated as a pill, dragee, capsule, liquid, gel, syrup, slurry, or suspension.

In the present invention, the pharmaceutical composition can be formulated or used in combination with one or more drugs selected from the group consisting of calcium channel blockers, antioxidants, glutamate antagonists, anticoagulants, antihypertensive agents, antithrombotic agents, antihistamines, anti-inflammatory analgesics, anticancer agents, and antibiotics.

In addition, the present invention relates to a food or food additive containing aptamin C or a pharmaceutically acceptable salt thereof, which has an effect of preventing and improving degenerative brain diseases, as an active ingredient.

The functional food of the present invention can be used in various ways such as drugs, foods and beverages for preventing inflammation. Functional foods of the present invention include, for example, various foods, candy, chocolate, beverages, gum, tea, vitamin complexes, dietary supplements, and the like, and may be used in the form of powders, granules, tablets, capsules or beverages.

Aptamin C is comprised as an active ingredient in the functional food of the present invention has excellent oxidative stress inhibitory activity, so it will be apparent to those skilled in the art that it exhibits excellent efficacy when used in food.

Compositions comprising the compounds according to the present invention are formulated in the form of oral dosage forms such as powders, granules, tablets, capsules, suspensions, emulsions, syrups, aerosols, etc., external preparations, suppositories, and sterile injectable solutions according to a conventional method. Carriers, excipients, and diluents that may be used in the same manner as lactose, dextrose, sucrose, sorbitol, mannitol, xylitol, erythritol, maltitol, starch, gum acacia, alginate, gelatin, calcium phosphate, calcium Silicate, cellulose, methyl cellulose, microcrystalline cellulose, polyvinyl pyrrolidone, water, methylhydroxybenzoate, propyl-hydroxybenzoate, magnesium stearate and mineral oil. In the case of formulation, it is prepared using diluents or excipients such as fillers, extenders, binders, wetting agents, disintegrants, and surfactants that are usually used. Solid preparations for oral administration include tablets, pills, powders, granules, capsules, etc., and these solid preparations comprise at least one or more excipients in the compound, at least cotton, starch, calcium carbonate, and sucrose. Alternatively, it is prepared by mixing lactose, gelatin, and the like. In addition to simple excipients, lubricants such as magnesium stearate and talc are also used. Liquid preparations for oral use include suspensions, liquid solutions, emulsions, syrups, etc. In addition to water and liquid paraffin, which are commonly used simple diluents, various excipients such as wetting agents, sweetening agents, fragrances, and preservatives may be included. Preparations for parenteral administration include sterilized aqueous solutions, non-aqueous solutions, suspensions, emulsions, lyophilized preparations, and suppositories. As the non-aqueous solvent and suspending agent, propylene glycol, polyethylene glycol, vegetable oil such as olive oil, and injectable ester such as ethyl oleate may be used. As a base for suppositories, witepsol, macrogol, tween 61, cacao butter, laurin paper, glycerogelatin, and the like may be used.

The preferred dosage of the compound of the present invention varies depending on the condition and weight of the patient, the degree of disease, the form of the drug, the route and duration of administration, but may be appropriately selected by those skilled in the art. However, for a desirable effect, the compound is preferably administered at 0.0001 mg/kg to 1 g/kg per day, preferably 0.001 mg/kg to 0.1 g/kg. Administration may be administered once a day, or may be divided several times. Therefore, the dosage does not limit the scope of the present invention in any way.

In addition, the present invention provides a health functional food for preventing and improving degenerative brain diseases comprising aptamin C or a pharmaceutically acceptable salt thereof as an active ingredient.

The health functional food containing the compound of the present invention can be variously used for drugs, foods and beverages for the prevention and improvement of degenerative brain diseases. Food forms to which the compound of the present invention can be added include various foods such as candy, beverages, gums, tea, vitamin complexes, or foods that are health supplements.

The compounds of the present invention may be added to food or beverages for the purpose of preventing and improving degenerative brain diseases. At this time, the amount of the compound in the food or beverage may generally be added to the health food composition of the present invention in 0.01 to 15% by weight of the total food weight, and the health drink composition may be added in a ratio of 0.02 to 10 g, preferably of 0.3 to 1 g based on 100 ml. The health beverage composition of the present invention has no particular limitation on the liquid component except for containing the aptamin C of the present invention as an essential component in the indicated ratio, and it can comprise various flavoring agents or natural carbohydrates, etc. as additional component Examples of the above-described natural carbohydrates are monosaccharides such as glucose and fructose disaccharides such as maltose, sucrose, and the like, and polysaccharides such as dextrin, cyclodextrin, and the like. These are the sugars and sugar alcohols such as xylitol, sorbitol, and erythritol. As flavoring agents other than those described above, natural flavoring agents (taumatin, stevia compounds (for example, rebaudioside A, glycyrrhizin, etc.) and synthetic flavoring agents (saccharin, aspartame, etc.) can be advantageously used. The proportion of the natural carbohydrate is generally about 1 to 20 g, preferably about 5 to 12 g per 100 ml of the composition of the present invention. In addition to the above, the composition of the present invention may be included various nutrients, vitamins, minerals (electrolytes), flavoring agents such as synthetic flavors and natural flavoring agents, coloring agents and heavy weight agents (cheese, chocolate, etc.), pectic acid and salts thereof, alginic acid and its salts, organic acids, protective colloidal thickeners, pH adjusters, stabilizers, preservatives, glycerin, alcohols, or carbonates used in carbonated beverages.

In addition, the compositions of the present invention may comprise natural fruit juice and flesh for the production of fruit juice beverages and vegetable beverages. These components may be used independently or in combination. The proportion of these additives is not so critical, but is generally selected in the range of 0 to about 20 parts by weight per 100 parts by weight of the composition of the present invention.

The composition of the present invention comprises 0.01 to 99% by weight of the compound based on the total weight of the composition. However, the composition as described above is not necessarily limited thereto, and may change according to the patient's condition and the type and progression of the disease.

The composition comprising the compound of the present invention may further include an appropriate carrier, excipient, and diluent commonly used in the preparation of pharmaceutical compositions.

Advantageous Effects

As can be seen through the present invention, the composition comprising the complex of vitamin C and aptamer binding to vitamin C of the present invention as an active ingredient exhibits a neuroprotective effect, so it is useful as a prevention or treatment for degenerative brain diseases.

DESCRIPTION OF DRAWINGS

FIGS. 1-3 is a diagram schematically showing ascorbic acid-based SELEX, and FIG. 1 shows that vitamin C has a reduced form of L-ascorbic acid and an oxidized form of L-dehydroascorbic acid (DHA). FIG. 2 shows that, L-ascorbic acid is rapidly oxidized to DHA and loses its antioxidant ability and AptaminC3T31, an aptamer that prevents the oxidation of L-ascorbic acid, was discovered through L-ascorbic acid-based SELEX, and FIG. 3 is a diagram showing the binding of Ascorbic acid and AptaminC3T31. The complex of Ascorbic acid and AptaminC3T31 is referred to as NXP031, FIGS. 4-5 is a diagram showing a fluorescence-based microplate assay that inhibits ascorbic acid oxidation, and FIG. 4 is an experimental result using OPDA, a substance that becomes fluorescent by binding to DHA. Under the conditions that ascorbic acid is treated with hydrogen peroxide to oxidize ascorbic acid, the addition of AptaminC3T31 oxidation of ascorbic acid is prevented. FIG. 5 is a comparison of the antioxidant activity of remaining ascorbic acid using DCPIP after AptaminC3T31+ascorbic acid and ascorbic acid were left for 8 weeks under the same conditions. AptaminC3T31+ascorbic acid maintained 50% antioxidant activity even after 8 weeks, FIGS. 6-7 is a picture showing the characteristics of the ITC (Isothermal Titration calorimetry) of the aptamer of the present invention that binds to ascorbic acid, FIG. 6 shows raw data showing the heat generated from each titration of ascorbic acid, FIG. 7 shows the combined heat of each titration after correction for the diluted heat of the titrant. The binding affinity between the aptamer and ascorbic acid of the present invention is 0.9 μM, FIGS. 8-14 are diagrams showing the neuroprotective effect of NXP031 on the MPTP-induced PD mouse model. adult C57BL/6 mice were administered intraperitoneally (4 times, 2 h intervals) of 20 mg/kg MPTP, NXP031 (4 mg AptaminC3T31/kg and 200 mg ascorbic acid/kg body weight) or saline solution was injected intraperitoneally, FIG. 8 is a diagram summarizing the overall experimental process, after intraperitoneal administration of 20 mg/kg MPTP (4 times, 2 h intervals) to adult C57BL/6 mice to induce destruction of dopamine neurons, and then NXP031 (4 mg AptaminC3T31/kg and 200 mg ascorbic acid/kg body weight) was injected intraperitoneally to confirm the neuroprotective effect of NXP031, and behavioral experiments (Pole test, Rotarod test) were conducted on day 4, and sacrifice was performed on day 5 and analyzed with staining midbrain dopamine neurons, FIG. 9 is a diagram showing that there is no significant difference in body weight between groups, FIGS. 10 and 11 are diagrams showing the results of the Pole test and the Rotarod test performed 3 days after the final MPTP administration, respectively. As a result of the Pole test, the experimental group treated with NXP031 was superior to the experimental group treated with Vitamin C and AptaminC3T31 alone, respectively. And it can be seen that the recovery was not significantly different from that of Sham without MPTP treatment, and the statistical significance was indicated by markers (*$P<0.02$ vs sham; #$P<0.05$ vs Vehicle). As a result of the Rotarod test, it can be seen that the experimental group treated with NXP031 was superior to the experimental group treated with Vitamin C and AptaminC3T31 alone, respectively, and the statistical significance was indicated by markers (*$P<0.02$ vs sham; #$P<0.05$ vs Vehicle), FIG. 12 is a result of confirming the dopaminergic neurons of striatum and substantia nigra using immunohistochemical staining with an anti-TH antibody, and the number of TH-positive neurons was counted by three-dimensional analysis. Data are expressed as mean±S.E.M. of at least three independent experiments, and statistically significant difference markers (*$P<0.02$ vs Control; #, § $P<0.05$ vs MPTP), FIG. 13 is a result of Striatal optical density measurement, which was significantly increased than the vehicle only in NXP031, FIG. 14 shows the number of TH-positive dopaminergic neurons in the SN. When counting the total TH-positive cells in the SN, it can be seen that the destruction of the TH positive cells by MPTP in NXP031 is mostly protected.

In this drawings, the aptamer binding to vitamin C (ascorbic acid) was named aptamin C, and in particular, the aptamin C used in the examples was represented as AptaminC3T31, and the AptaminC3T31 and vitamin C complex of the present invention was named NXP031.

MODE FOR INVENTION

Hereinafter, the present invention will be described in more detail by the following examples. However, the following examples are described with the intention of illustrating the present invention, and the scope of the present invention is not to be construed as being limited by the following examples.

Example 1: DNA Aptamer Selection and Sequence Analysis

Ascorbic Acid SELEX:

9 rounds of SELEX for ascorbic acid were performed using a DNA library (BasePair Biotechnologies) consisting of ~$10^{15}$ unique oligonucleotides. The buffer composition used was as follows: 50 mM Sodium Acetate pH 5.5 (Sigma), 1 mM $MgCl_2$ (Sigma), 0.05% Tween 20 (Sigma), 1% BSA (Sigma) and 1 mM glutathione (Sigma). The stringency of SELEX was changed by reducing the binding time of the aptamer to the target, changing the buffer composition, and reducing the concentration of the target in free molecule elution. Negative selection for DHA was performed to remove aptamers that bind to oxidized form of Ascorbic acid from the enriched library (FIG. 2).

Bioinformation analysis of the rich library produced by the SELEX method obtained candidate aptamers, and the ability to protect AA from oxidation from these top 20 was screened. The aptamer of SEQ ID NO: 1 showed the best effect.

Example 2: Fluorescence Analysis of Ascorbic Acid Oxidation Products

The oxidation of ascorbic acid was measured in reverse with detecting the oxidized product dehydroascorbic acid (DHA) with modifying a method described in Vislisel et al. (Vislisel, J. M. Schafer, F. O. and Buettner, G. R. (2007) Analytical biochemistry, 365, 31-39).

Briefly, aptamers were incubated with AA (10.3 μM) at 4× concentration for 30 minutes at room temperature before addition of 25 μM $H_2O_2$ (Sigma). Before the addition of OPDA dye (Sigma), the oxidizing agent sample was added and incubated at room temperature for 10 minutes. Immediately after addition of the dye (954.6 μM) sample, and read at excitation 345 nm; emission: 425 nm with a SpectraMax® plate reader (Molecular Devices) for 45 minutes at intervals of 60 seconds until the control converges. To confirm that the screening data shows AA protection and that there is no interference of oxidation products (DHA) or analytical dyes (OPDA), fluorescence analysis was repeated with DHA (10.3 µM) (Sigma) with selected aptamers cultured in place of AA. All analyzes were performed by calibrating with 50 mM sodium acetate (Sigma), 1% BSA (Sigma), 0.05% Tween 20 (Sigma), and 1 mM $MgCl_2$ (Sigma) pH 5.5. All fluorescence assays were performed in black 384-well plates (greiner bio-one). Each sample was repeated three times (FIG. 4).

Example 3: Increased Storage of Vitamin C by Aptamer

The aptamin C of the present invention was maintained at room temperature for 8 weeks and the reducing activity of ascorbic acid was measured using DCPIP (2,6-Dichlorophenolindophenol). As can be seen from FIG. 5, the aptamine C of the present invention inhibits the oxidation of ascorbic acid and maintains the reducing power, thereby increasing the shelf life by 4 times or more compared to the control group in which ascorbic acid alone exists.

Example 4: Aptamer Titration for AA

It was titrated against AA (10.3 µM) to determine the effective concentration of the optimal aptamer (A). The relative concentrations of aptamers for AA were 10×, 5×, 2×, 1×, 0.5×, 0.25× and 0.1×. All aptamer/AA mixtures were incubated at room temperature for 30 minutes before the addition of 10.3 µM $CuSO_4$, and the samples were incubated at room temperature for another 10 minutes before addition of 954.6 µM OPDA. Plate ex: 345 nm; em: Read plate at ex: 345 nm; em: 425 nm for 45 minutes, and data were collected every 60 s. Each sample was run in triplicate. As can be seen in FIG. 7, the binding affinity between the aptamer and ascorbic acid of the present invention is 0.9 µM,

Example 5: Effect of Complex of Aptamin C and Vitamin C on $MPP^+$-Induced Cytotoxicity SH-SY5Y cells (human neuroblastoma) were treated with MPP (1-methyl-4-phenylpyridinium) at the indicated concentration, and then cell viability was measured, and the cells were pre-treated with NXP031 (aptamer and vitamin C complex of the present invention) for 1 hour, and then exposed with 5 mM MPP for 24 hours, and then the cell viability was measured. The cell viability was measured by MTT assay.

Example 6: Effects on MPTP-Induced Parkinson's Disease Mouse Model 1-1. Parkinson's Disease Mouse Model
Parkinson's disease was acutely induced with intraperitoneal injection of 20 mg/kg of MPTP (1-methyl-4-phenyl-1,2,3,6-tetrahydropyridine) at 2 hour intervals for a total of 4 consecutive days to 8-week-old C57BL/6 mice weighing 25 g or more.

1-2. Preparation and Administration of the Composition
A composition was prepared by mixing 200 mg/kg body weight of vitamin C and 4 mg of an aptamer binding to the vitamin C (GTGGA GGCGG TGGCC AGTCT CGCGG TGGCG GC; SEQ ID NO: 1)/kg body weight. 1 hour after the end of the last MPTP administration to the mouse inducing Parkinson's disease by the above method, the composition was diluted to a final dose of 200 mg of vitamin C/kg body weight and 4 mg of aptamin C/kg body weight and 50 µl of the resulting diluent was administered orally or intraperitoneally in the mouse. The single administration of vitamin C and aptamin C was administered intraperitoneally or orally with 50 µl at the same concentration as in the above composition. The administration of composition and vitamin C and aptamin C were performed once a day for 4 consecutive days.

1-3. Neurobehavioral Evaluation
In order to evaluate the neurobehavioral effect induced by the MPTP and composition administered by the above method, a pole test and a rotarod test were performed 4 days after Parkinson's disease was induced by the method described above.

A pole test was conducted using a 55 cm high pole. The mouse was placed above the pole to measure the time to come down to the floor.

Rota rod test starts with a speed of 2.5 rpm with the mouse on the rota rod treadmill, and then gradually increases the speed so that the maximum speed is 25 rpm (3.5 to 35 rpm in the case of high speed), and when the treadmill rotates, the time (seconds) until the mouse loses its balance and falls to the floor was measured.

1-4. Brain Tissue Immunohistochemical Staining
A section of the brain tissue obtained by the above method was reacted with 1% hydrogen peroxide for 15 minutes to remove the activity of endogenous peroxidase. Next, tyrosine hydroxylase antibody diluted to an appropriate concentration was added and stained overnight at 4° C. After washing and removing the unbound primary antibody, stain with biotinylated secondary antibody for 90 minutes at room temperature. After washing and removing unbound secondary antibody, it is stained with ABC solution for 1 hour at room temperature. After color reaction with 3,3-diaminobenzidine, it was observed under a microscope.

As can be seen from FIGS. 10 to 14, in the experiment result, the MPTP-induced Parkinson's disease mouse model test, it was confirmed that the deficit of exercise capacity was behaviorally reduced by the treatment of the composition (vitamin C and aptamin C) of the present invention. In addition, as a result of confirming the dopaminergic neurons in the tissue through immunohistochemical staining for tyrosine hydroxylase in the brain tissue sections obtained from the mice to which the sample was administered, it was confirmed that the apoptosis of dopaminergic neurons was significantly reduced in the composition-administered group.

The invention claimed is:

1. A composition for the treatment and prevention of degenerative brain diseases comprising an aptamer consisting of the nucleotide sequence of SEQ ID: 1 and vitamin C.

2. The composition for treating and preventing degenerative brain diseases according to claim 1, wherein the mixing ratio of vitamin C and aptamer is in the range of 10:1 to 500:1 by weight.

3. The composition for treating and preventing degenerative brain diseases according to claim 1, wherein the composition has a neuronal protective effect.

4. The composition for treating and preventing degenerative brain diseases according to claim 1, wherein the degenerative brain disease is selected from the group consisting of stroke, dementia, Alzheimer's disease, Parkinson's disease, Huntington's disease, multiple sclerosis and amyotrophic lateral sclerosis.

5. The composition for treating and preventing degenerative brain disease according to claim 4, wherein the degenerative brain disease is Parkinson's disease.

* * * * *